US009416097B2

(12) United States Patent
Mendes et al.

(10) Patent No.: US 9,416,097 B2
(45) Date of Patent: Aug. 16, 2016

(54) CRYSTALLINE MINOCYCLINE BASE AND PROCESSES FOR ITS PREPARATION

(75) Inventors: Zita Mendes, Lisbon (PT); Jose Rafael Antunes, Setubal (PT); Susana Marto, Costa da Caparica (PT); William Heggie, Pamela (PT)

(73) Assignee: Hovione Scientia Limited, Co. Cork (IE)

( * ) Notice: Subject to any disclaimer, the term of this patent is extended or adjusted under 35 U.S.C. 154(b) by 7 days.

(21) Appl. No.: 13/599,116

(22) Filed: Aug. 30, 2012

(65) Prior Publication Data

US 2013/0030195 A1 Jan. 31, 2013

Related U.S. Application Data

(62) Division of application No. 12/528,209, filed as application No. PCT/GB2008/000625 on Feb. 22, 2008, now Pat. No. 8,258,327.

(30) Foreign Application Priority Data

Feb. 23, 2007 (PT) ........................................ 103661

(51) Int. Cl.
C07C 237/26 (2006.01)
(52) U.S. Cl.
CPC .................................... *C07C 237/26* (2013.01)
(58) Field of Classification Search
None
See application file for complete search history.

(56) References Cited

U.S. PATENT DOCUMENTS

| 3,148,212 | A | | 9/1964 | Boothe et al. | |
|---|---|---|---|---|---|
| 3,226,436 | A | | 12/1965 | Petisi et al. | |
| 4,849,136 | A | | 7/1989 | Saito et al. | |
| 5,262,173 | A | * | 11/1993 | Sheth et al. | 424/494 |
| 8,258,327 | B2 | | 9/2012 | Marto et al. | |
| 2010/0286417 | A1 | | 11/2010 | Mendes et al. | |

FOREIGN PATENT DOCUMENTS

| WO | 99/32118 A1 | | 7/1999 |
|---|---|---|---|
| WO | WO99/32118 | * | 7/1999 |
| WO | 2007014154 A2 | | 2/2007 |
| WO | 2008102161 A2 | | 8/2008 |

OTHER PUBLICATIONS

Church et al. In Journal of Organic Chemistry 36(5) 723-25 (1971).*
Martell et al. In Journal of Medicinal Chemistry 10, 44-46 (1967).*
Broadhead et al. In WO01/31339 A1 (published: May 3, 2001).*
Ambike et al. In Pharmaceutical Research, 22(6), 990-998 (2005).*
Bernardi et al. In II Farmico 30(9) pp. 736-741 (1975).*
Yu, L. In Advanced Drug Delivery Reviews 48, 27-42 (2001).*
Bernardi et al., "Tetracycline Derivatives," Il Farmaco Edizione Scientifica, 1975, vol. 30, No. 9, pp. 736-741.
Brittain et al., "Chapter 1: Theory and Principles of Polymorphic Systems and Chapter 6: Structural Aspects of Polymorphism" Polymorphism in pharmaceutical solids, 1999, (Chapter 1) pp. 1-10 and (Chapter 6) pp. 185-227.
Byrn et al., "Pharmaceutical Solids: A Strategic Approach to Regulatory Considerations," Pharmaceutical Research, 1995, vol. 12, No. 7, pp. 945-954.
Caira, "Crystalline Polymorphism of Organic Compounds," Topics in Current Chemistry, 1998, vol. 198, pp. 163-208.
Chinese First Office Action, Application No. 200880005932.8, dated Apr. 28, 2012.
Chinese Second Office Action, Application No. 200880005932.8, dated Nov. 13, 2012.
Church et al., "Synthesis of 7-Dimethylamino-6-demthyl-6-deoxytetracycline (Minocycline) via 9-Nitro-6-demethyl-6-deoxytetracycline," Journal of Organic Chemistry, 1971, vol. 36, No. 5, pp. 723-725.
Israeli Office Action, Application No. 200544, dated Jul. 29, 2012.
Norris, "Chapter 1: Laboratory Methods," Experimental Organic Chemistry, 1924, 2nd Edition, pp. 1-5.
PCT International Preliminary Report on Patentability, Application No. PCT/GB2008/000625, dated Sep. 3, 2009.
PCT International Search Report, Application No. PCT/GB2008/000625, dated Nov. 25, 2008.
PCT Written Opinion, Application No. PCT/GB2008/000625, dated Nov. 25, 2008.
Russian Office Action, Application No. 2009135403, dated Jul. 16, 2012.
Yu, "Amorphous pharmaceutical solids: preparation, characterization and stabilization," Advanced Drug Delivery Reviews, 2001, vol. 48, pp. 27-42.
Pearson et al., "Stability and compatibility of minocycline hydrochloride and rifampin in intravenous solutions at various temperatures", American Journal of Hospital Pharmacists, 1993, vol. 50, pp. 698-702.
Ambike et al., "Spray-Dried Amorphous Solid Dispersions of Simvastatin, a Low Tg Drug: in Vitro and in Vivo Evaluations", Pharmaceutical Research, 2005, vol. 22, No. 6, pp. 990-998.
Broadhead et al., "The Spray Drying of Pharmaceuticals", Drug Development and Industrial Pharmacy, 1992, vol. 18, Nos. 11 & 12, pp. 1169-1206.
Martell et al., "The 6-Deoxytetracyclines. VII. Alkylated Aminotetracyclines Possessing Unique Antibacterial Activity", Journal of Medicinal Chemistry, 1967, vol. 10, pp. 44-46.
Mexican Office Action, Application No. MX/a/2012/005474 dated Feb. 11, 2016, English translation.

* cited by examiner

*Primary Examiner* — Dennis Heyer
(74) *Attorney, Agent, or Firm* — MacMillan, Sobanski & Todd, LLC

(57) ABSTRACT

The invention provides crystalline minocycline base. In particular, three crystalline polymorphic forms, designated Form I, Form II and Form III, of minocycline base are provided. These are characterized by XRD and IR data. Processes for preparing the new polymorphic forms are also provided. For example, Form I is prepared by dissolving and/or suspending amorphous minocycline base in an organic solvent chosen from ethers followed by crystallization from the mixture.

5 Claims, 8 Drawing Sheets

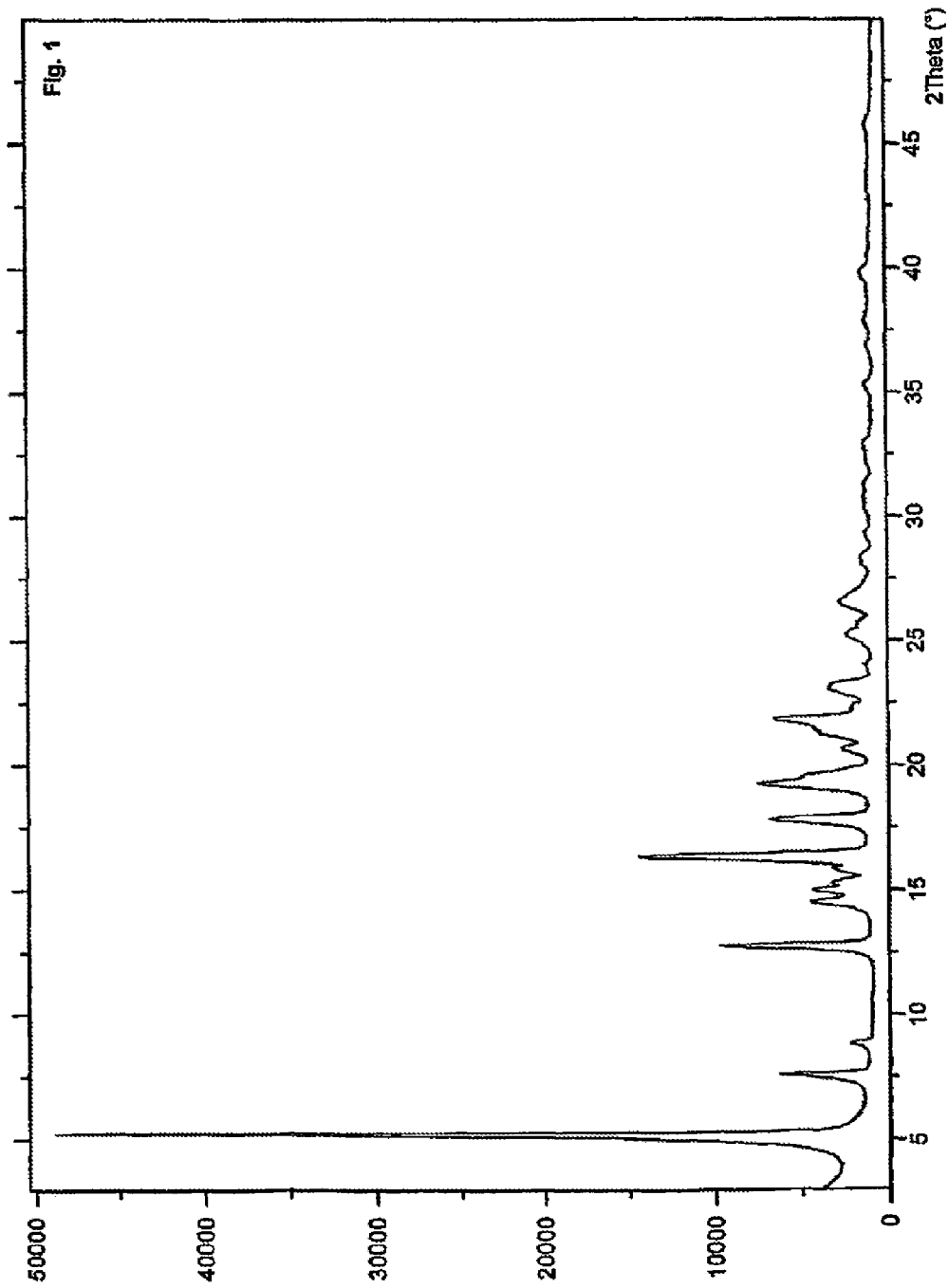
Form I – X-ray Fig. 1

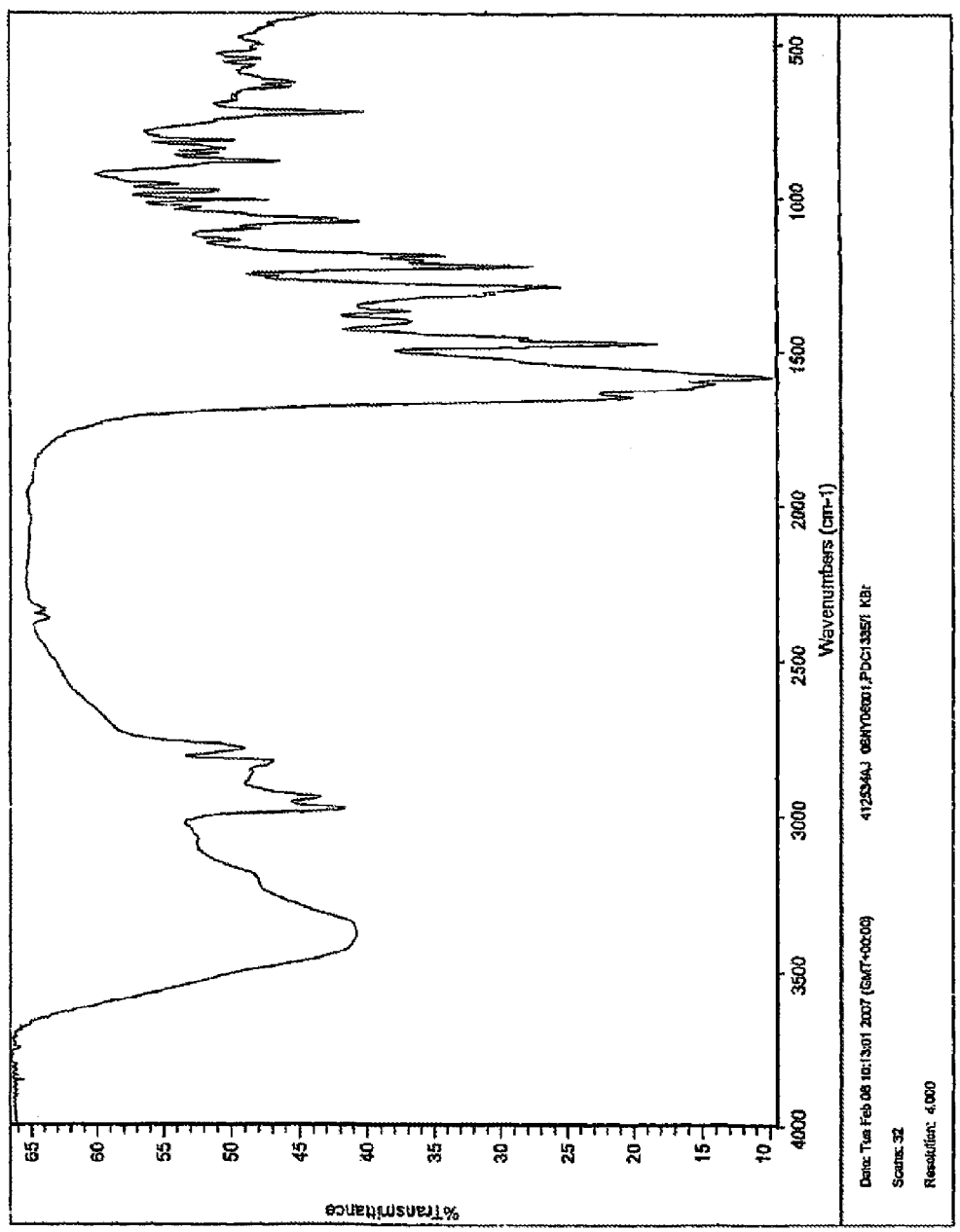
Form I – IR Fig.2

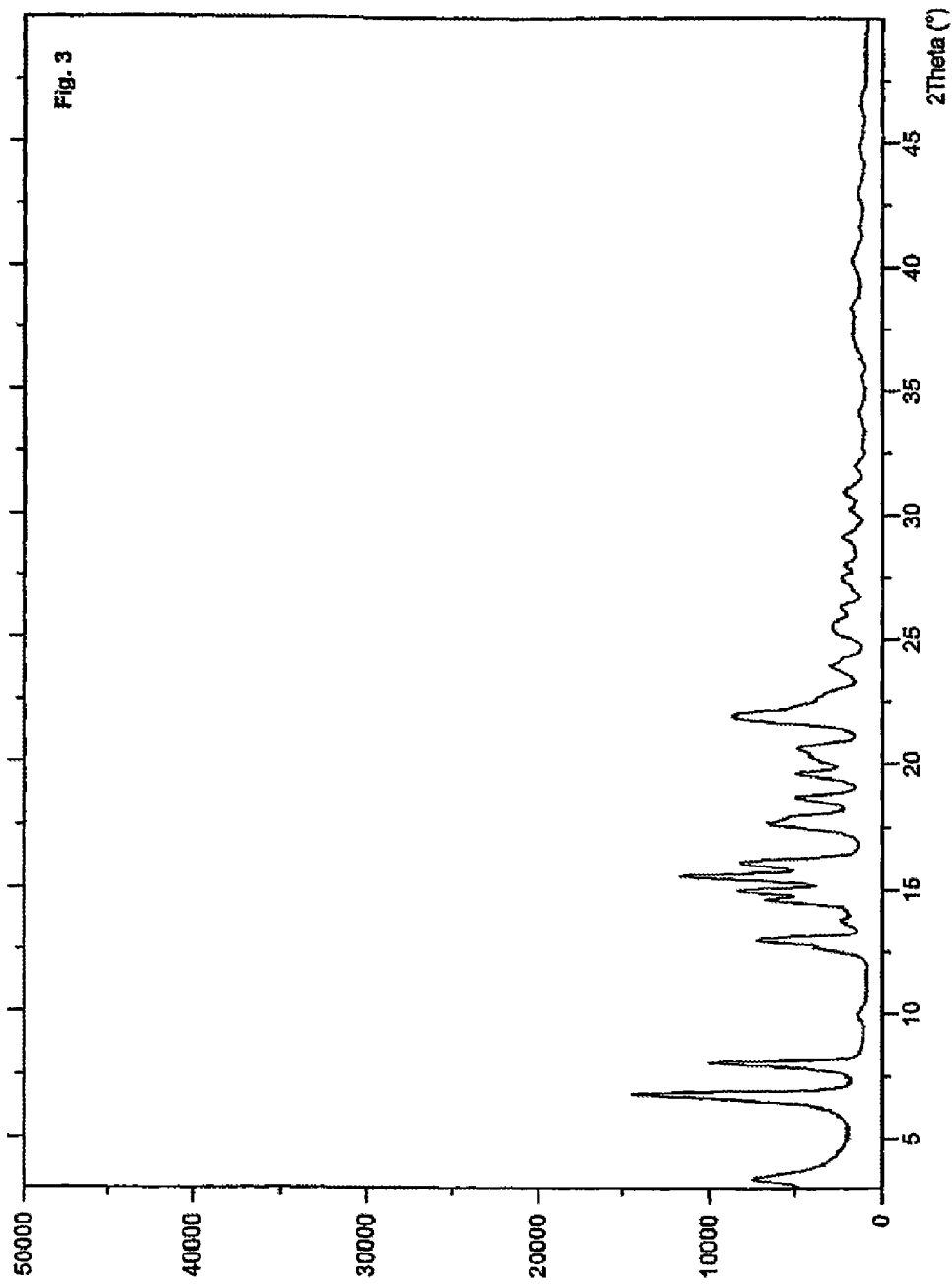

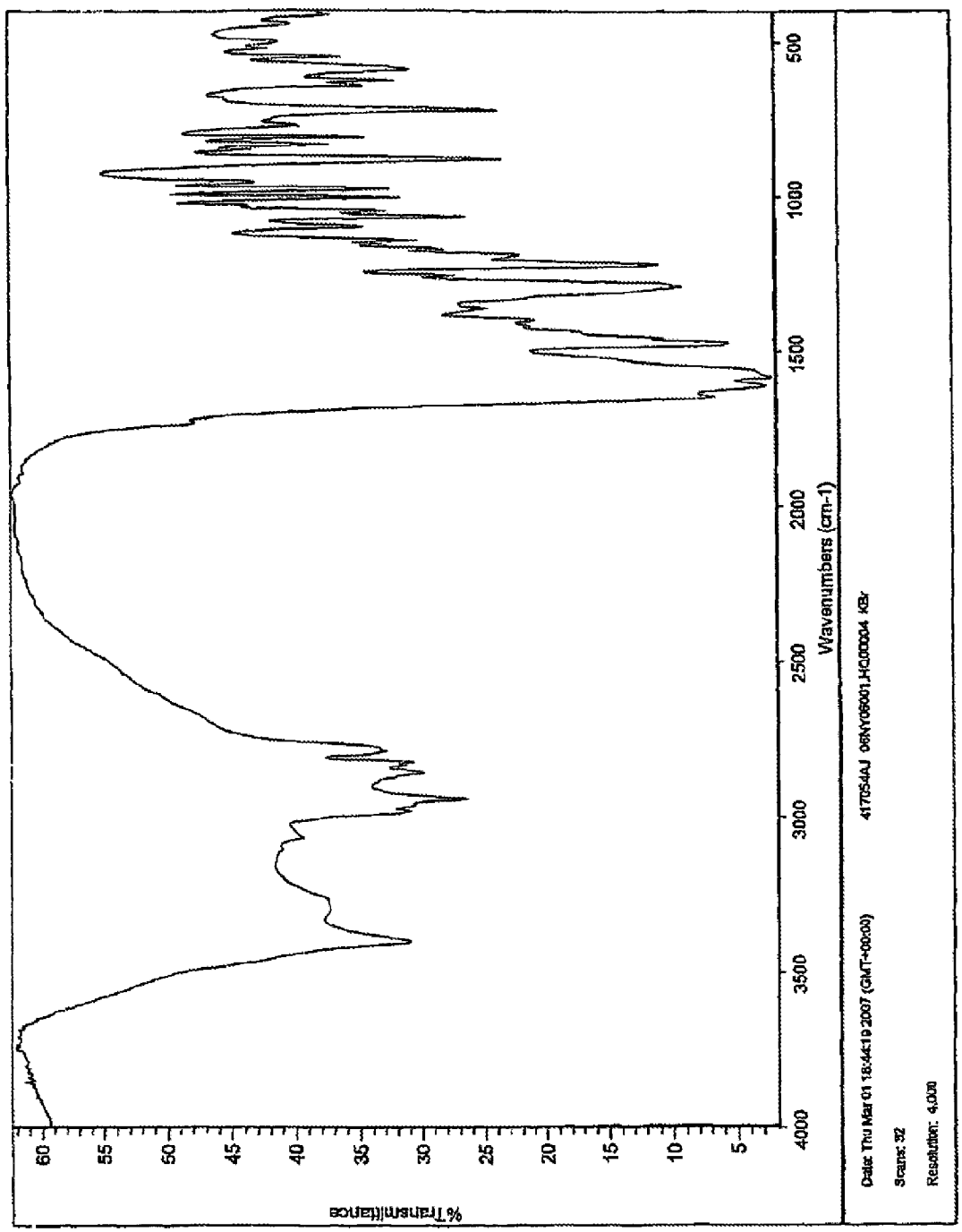

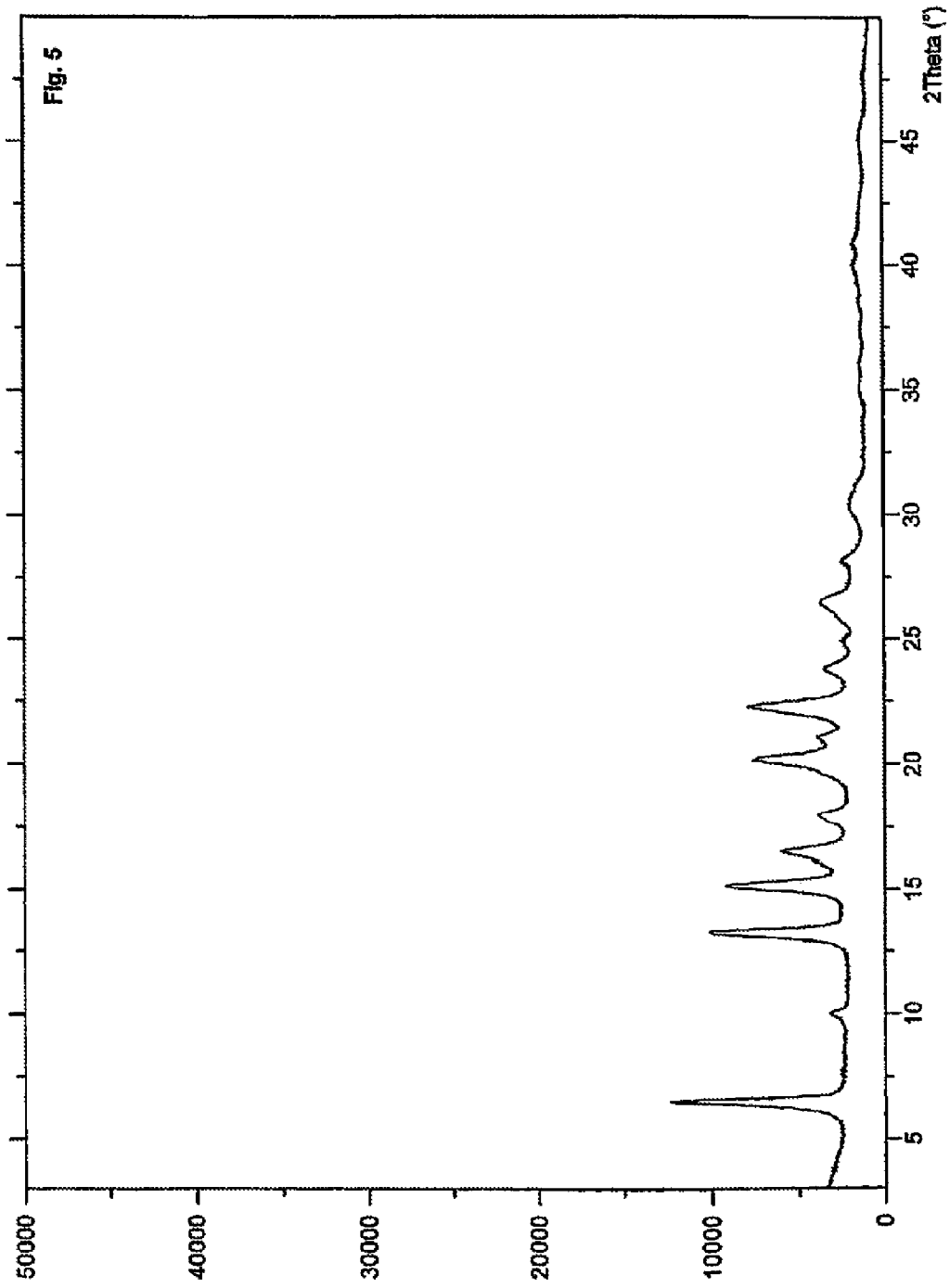

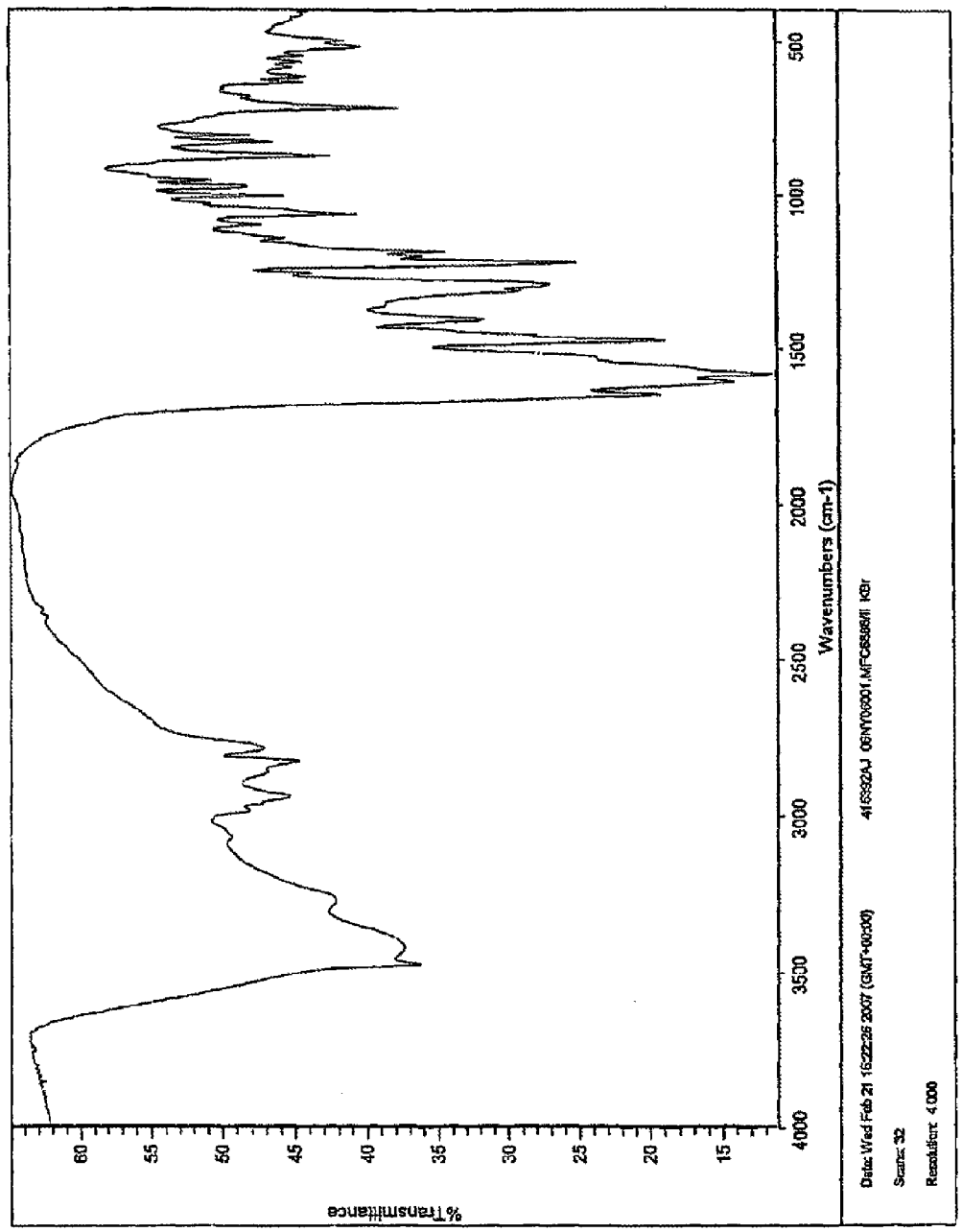
Form III – IR Fig.6

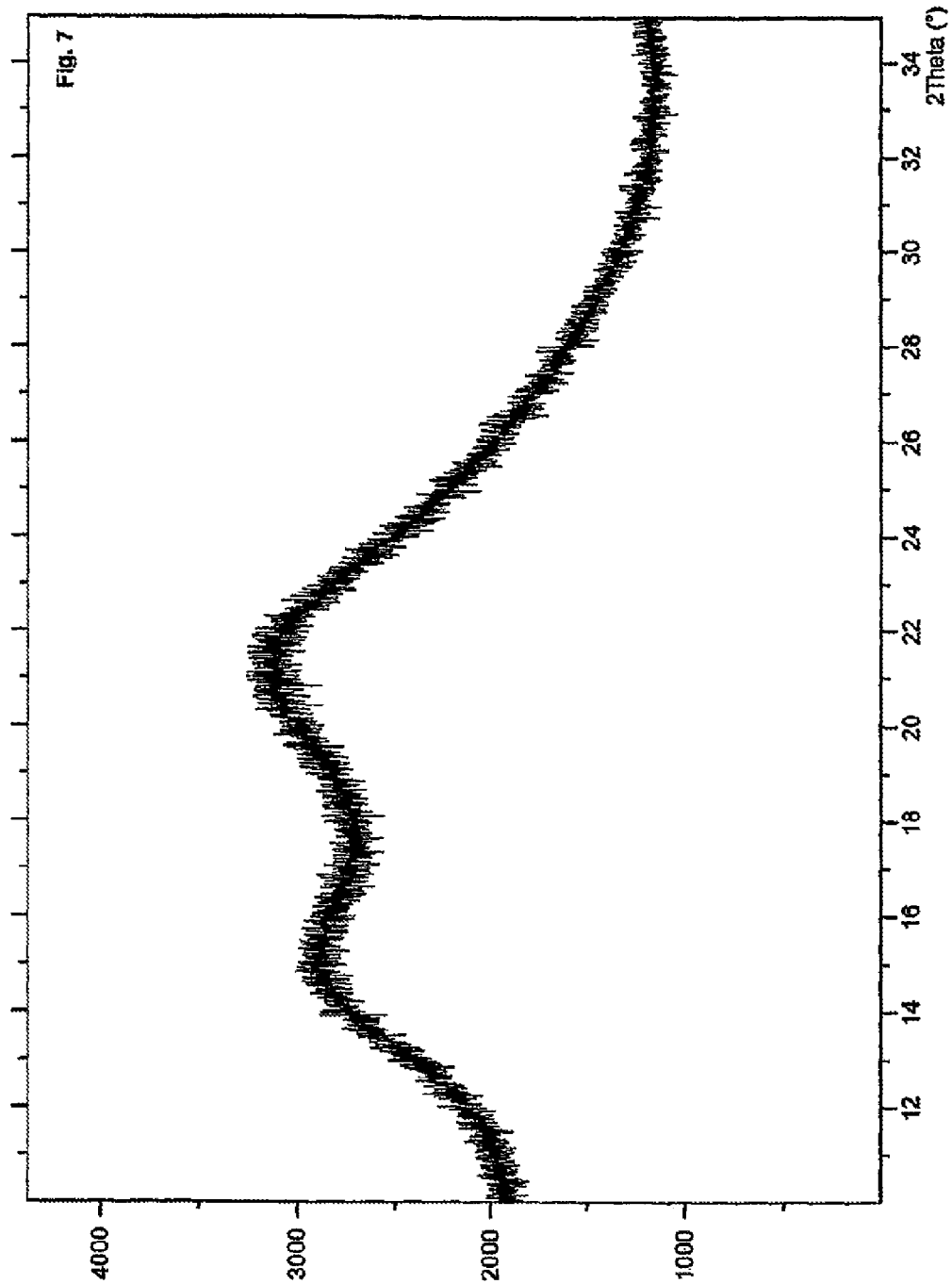

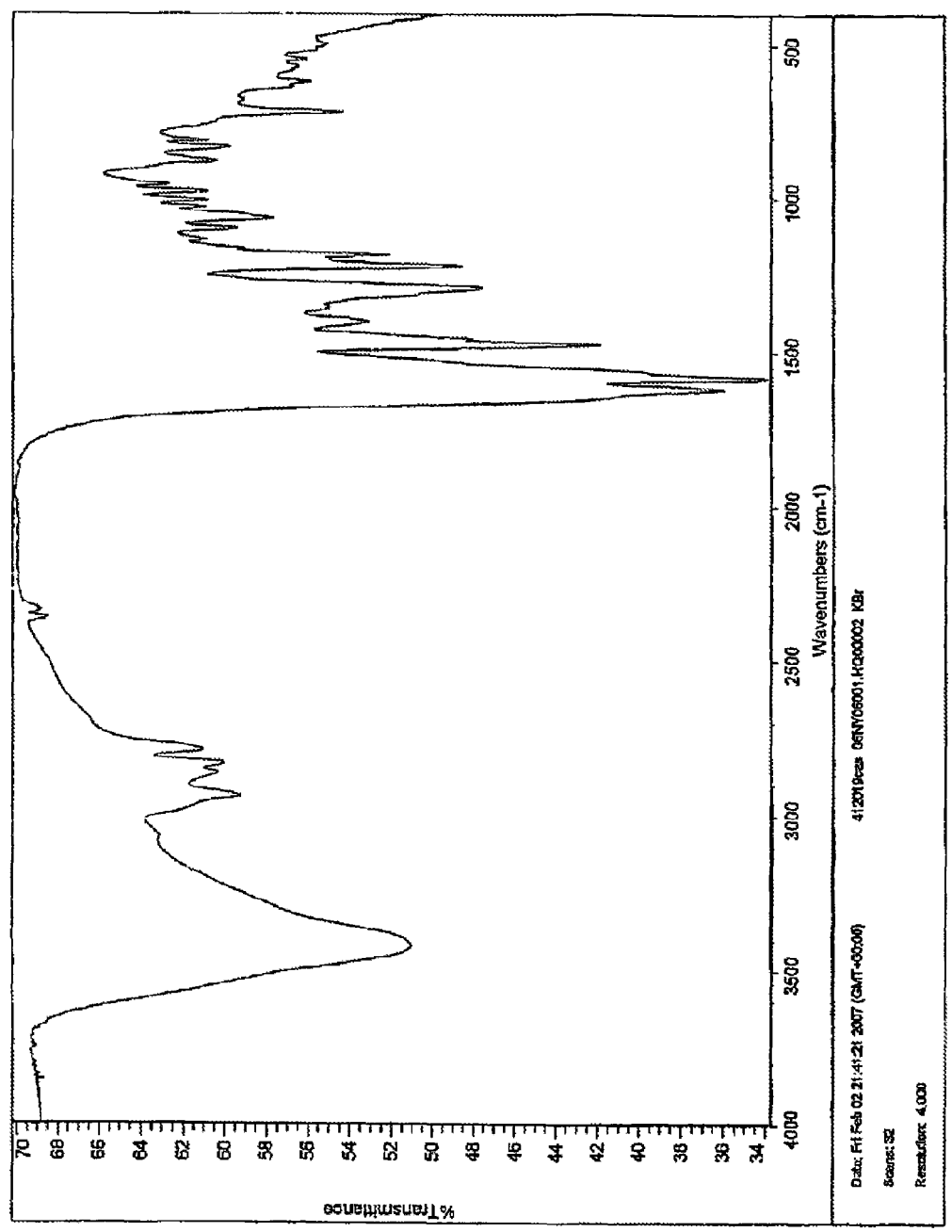

CRYSTALLINE MINOCYCLINE BASE AND PROCESSES FOR ITS PREPARATION

CROSS-REFERENCE TO RELATED APPLICATIONS

This application is a divisional application of U.S. Ser. No. 12/528,209 filed, Nov. 4, 2009, now U.S. Pat. No. 8,258,327 issued Sep. 4, 2012, which is a national stage application filed under 35 USC §371 of international application PCT/GB08/00625 file Feb. 22, 2008, which claims the priority to PT 103661 filed Feb. 23, 2007, the entire disclosures of which are expressly incorporated herein by reference

DESCRIPTION

The present invention provides crystalline minocycline base including three new polymorphic forms thereof, and also describes a process to obtain pure minocycline base in a crystalline form wherein all the impurities are controlled, especially the impurity 4-epi minocycline, to very low levels.

BACKGROUND OF THE INVENTION

Minocycline is a member of the broad spectrum tetracycline antibiotics, which has a broader spectrum than the other members of this group of compounds.

Minocycline is widely used in therapy, primarily to treat acne and rosacea at a once daily dose of 100 mg.

The preparation of minocycline is disclosed in U.S. Pat. No. 3,148,212; U.S. Pat. No. 3,226,436 and U.S. Pat. No. 4,849,136.

Minocycline may be used as base per se or as non-toxic acid addition salts of organic or inorganic acids, e.g., sulfonic, trichloroacetic or hydrochloric acid.

Minocycline base, previously known before this invention only in the amorphous form, is not as stable as the corresponding acid addition salts and hence, methods to provide a stable form of minocycline base which makes its use promising as an active ingredient have been examined.

BRIEF DESCRIPTION OF THE DRAWINGS

FIG. 1: X-ray diffraction pattern of crystalline Form I of minocycline base.

FIG. 2: Infrared spectrum of crystalline Form I of minocycline base.

FIG. 3: X-ray diffraction pattern of crystalline Form II of minocycline base.

FIG. 4: Infrared spectrum of crystalline Form II of minocycline base.

FIG. 5: X-ray diffraction pattern of crystalline Form III of minocycline base.

FIG. 6: Infrared spectrum of crystalline Form III of minocycline base.

FIG. 7: X-ray diffraction pattern of amorphous minocycline base.

FIG. 8: Infrared spectrum of amorphous minocycline base.

DETAILED DESCRIPTION

The present invention describes crystalline minocycline base, including new polymorphic forms of crystalline minocycline base and novel processes for their preparation.

The present inventors have now found that, surprisingly, minocycline base can in fact be provided in a stable crystalline form. They have also found three new polymorphic forms of crystalline minocycline base.

Accordingly, in its broadest aspect, the invention provides crystalline minocycline base.

In one aspect, polymorphic Form I of crystalline minocycline base is provided. That this is a crystalline form of minocycline base, which up until now has only been known in its amorphous form, is demonstrated by physical attributes whose application in this area is well known to those skilled in the art.

Crystalline Form I of minocycline base has a characteristic X-ray diffraction pattern shown in FIG. 1 and an infrared spectrum of FIG. 2.

Crystalline Form 1 is characterised by an X-ray diffraction pattern having peaks at 5.2, 7.6, 8.8, 12.8, 14.5, 15.0, 15.3, 15.9, 16.4, 17.8, 19.3, 19.5, 20.7, 21.3, 21.8, 22.3, 23.1, 24.0, 25.3, 25.7 and 26.5.+−.0.2°2.theta., as given in FIG. 1. It is further characterised by an infrared spectrum having peaks at 1646, 1602, 1581, 1470, 1397, 1364, 1286, 1218, 1182, 1134, 1072, 1061, 1023, 1001, 969, 950, 874, 850, 716, 636, 620 and 545.+−.4 cm.$^{-1}$ as given in FIG. 2.

In another aspect, the invention provides a process for the preparation of polymorphic Form I of crystalline minocycline base, which process comprises dissolving and/or suspending amorphous minocycline base in an organic solvent chosen from ethers followed by crystallization from the mixture.

Preferably, the process comprises suspending amorphous minocycline base in an organic solvent chosen from ethers, cooling the heterogeneous mixture to a temperature of from 0° C. to 30° C., the preferred range being from 10° C. to 15° C. and isolating Form I from the reaction mixture.

Any suitable ether solvent may be used, but is preferred to use methyl tert-butyl ether.

In another aspect, polymorphic Form II of crystalline minocycline base is provided. That this is a crystalline form of minocycline base, which up until now has only been known in its amorphous form, is demonstrated by physical attributes whose application in this area is well known to those skilled in the art.

Crystalline Form II of minocycline base has a characteristic X-ray diffraction pattern shown in FIG. 3 and an infrared spectrum of FIG. 4.

Crystalline Form II is characterised by an X-ray diffraction pattern having peaks at 3.4, 6.8, 8.0, 10.0, 13.0, 13.8, 14.6, 14.9, 15.5, 16.1, 17.6, 17.8, 18.6, 19.5, 20.2, 20.6, 21.9, 22.6, 23.9, 24.2, 25.4, 26.3, 27.1, 27.5, 28.0 and 29.1.+−.0.2°2.theta., as given in FIG. 3. It is further characterised by an infrared spectrum having peaks at 1644, 1607, 1582, 1469, 1453, 1413, 1396, 1358, 1287, 1251, 1217, 1186, 1166, 1136, 1061, 999, 970, 874, 716, 621 and 585.+−.4 cm.$^{-1}$, as given in FIG. 4.

In another aspect, a process for the preparation of polymorphic Form II of crystalline minocycline base comprises dissolving and/or suspending amorphous minocycline base in an organic solvent chosen from esters followed by crystallization from the mixture.

Preferably, the process comprises suspending amorphous minocycline base in an organic solvent chosen from esters, cooling the heterogeneous mixture to a temperature of from 0° C. to 30° C., the preferred range being from 10° C. to 15° C. and isolating the Form II from the reaction mixture.

Any suitable ester may be used as solvent, but it is preferred to use ethyl acetate.

In another aspect, polymorphic Form III of crystalline minocycline base is provided. That this is a crystalline form of minocycline base, which up until now has only been known in its amorphous form, is demonstrated by physical attributes whose application in this area is well known to those skilled in the art.

Crystalline Form III of minocycline base has a characteristic X-ray diffraction pattern shown in FIG. 5 and an infrared spectrum of FIG. 6.

Crystalline Form III is characterised by an X-ray diffraction pattern having peaks at 6.5, 10.0, 13.2, 15.1, 16.5, 17.9, 19.6, 20.2, 21.1, 22.3, 23.7, 24.8, 26.4, 28.1 and 30.5.+−.0.2°2.theta., as given in FIG. 5. It is further characterised by an infrared spectrum having peaks at 1647, 1605, 1581, 1470, 1399, 1307, 1286, 1251, 1216, 1195, 1179, 1136, 1094, 1058, 1024, 1000, 973, 950, 870, 825, 806, 716, 680, 634, 615, 584, 515, 496 and 413.+−.4 cm$^{-1}$, as given in FIG. 6.

In another aspect, a process for the preparation of polymorphic Form III of crystalline minocycline base comprises dissolving and/or suspending amorphous minocycline base in an organic solvent chosen from alcohols followed by crystallization from the mixture.

Preferably, the process comprises suspending amorphous minocycline base in an organic solvent chosen from alcohols, cooling the heterogeneous mixture to a temperature of from 0° C. to 30° C., the preferred range being from 10° C. to 15° C. and isolating the Form III from the reaction mixture.

Any suitable alcohol may be used a solvent, but it is preferred to use ethanol.

The crystalline minocycline bases in Forms I, II and III obtained by the processes described above have a high purity with all the impurities controlled, especially 4-epi minocycline, which is typically below 1.2% w/w (i.e., by weight of the base).

In another aspect, therefore, the invention provides crystalline minocycline base substantially free of 4-epi minocycline. By substantially free, we mean that no more than about 1.2% impurity by weight of the polymorph (w/w) is present. Preferably the impurity level is less than 1.2% w/w.

In a further aspect, therefore, the invention provides crystalline minocycline base comprising less than 1.2% w/w (by weight of the base) of 4-epi minocycline.

Another aspect of the invention provides processes for preparing amorphous minocycline base on an industrial scale, wherein the minocycline base is obtained in high purity, especially maintaining low levels of the content of 4-epi-minocycline.

In one aspect, there is provided a process for preparing amorphous minocycline base, which process comprises spray drying a solution or suspension of minocycline, in an organic solvent, preferably chosen from methyl tert-butyl ether, dichloromethane or isopropyl acetate A preferred process for preparing amorphous minocycline base comprises:

1) dissolving minocycline base in one or more organic solvents to form a solution or a suspension 2) spray drying the solution or suspension obtained in step 1)

3) optionally drying the amorphous minocycline base so obtained, if necessary under vacuum, at a temperature of from 25° C. to 45° C., preferably from 35° C. to 45° C.

Any suitable solvent may be used, and preferred solvents include methyl tert-butyl ether, dichloromethane or isopropyl acetate.

Any suitable technique for the spray drying may be used. For example, conventional spray drying techniques (as will be clear to those skilled in the art) may be employed.

EXAMPLES

The following examples are provided to illustrate the present invention and do not in any way limit its scope.

Example 1

Preparation of Form I of Crystalline Minocycline Base

Amorphous minocycline base (0.5 g) is suspended in methyl tert-butyl ether (4 ml) and the resulting heterogeneous mixture stirred for about 2 hours at a temperature between 0° C. and 30° C., preferably between 10° C. and 15° C.

The product is filtered, washed with methyl tert-butyl ether (1 ml) and dried under vacuum at about 45° C.-50° C. to yield crystalline minocycline base.

Yield: 0.38 g

The XRPD pattern and infrared are presented in FIG. 1 and FIG. 2.

4-epi minocycline: 0.06% in area (HPLC)

Melting point 113° C.

Example 2

Preparation of Form I of Crystalline Minocycline Base

Amorphous minocycline base (0.5 g) is dissolved in methyl tert-butyl ether (6 ml) and the resulting solution stirred at a temperature between 0° C. and 30° C., preferably between 10° C. and 15° C.

After about 5 minutes Form I of crystalline minocycline base precipitates from the solution.

The resulting suspension is filtered, washed with methyl tert-butyl ether (1 ml) and dried under vacuum at about 45° C.-50° C. to yield Form I of crystalline minocycline base.

Yield: 0.45 g.

Melting point: 113° C.

Example 3

Preparation of Form II of Crystalline Minocycline Base

Amorphous minocycline base (20 g) is suspended in ethyl acetate (160 ml) and the resulting heterogeneous mixture stirred for about 3 hours at a temperature between 0° C. and 30° C., preferably between 10° C. and 15° C.

The product is filtered, washed with ethyl acetate (10 ml) and dried under vacuum at about 45° C.-50° C. to yield crystalline minocycline base.

Yield: 17.4 g

HPLC purity: 99.5% in area 4-epi minocycline: 0.11% in area.

Melting point: 187° C.

The XRPD pattern and infrared are presented in FIG. 3 and FIG. 4.

Example 4

Preparation of Form II of Crystalline Minocycline Base

Amorphous minocycline base (5 g) is dissolved in ethyl acetate (40 ml) and the resulting solution stirred for about 3 hours at a temperature between 0° C. and 30° C., preferably between 10° C. and 15° C. whereupon Form II of crystalline minocycline base precipitated.

The product is filtered, washed with ethyl acetate (5 ml) and dried under vacuum at about 45° C.-50° C. to yield Form II of crystalline minocycline base.

Yield: 3.2 g
Melting point: 187° C.

Example 5

Preparation of Form III of Minocycline Base

Amorphous minocycline base (0.5 g) is suspended in ethyl alcohol (2.5 ml) and the resulting heterogeneous mixture stirred for at least 10 hours at a temperature between 0° C. and 30° C. preferably between 10° C. and 15° C.

The product is filtered, washed with ethyl alcohol (0.5 ml) and dried under vacuum at about 45° C.-50° C. to yield Form III of crystalline minocycline base.

Yield: 0.44 g

The XRPD pattern and infrared are presented in FIG. 5 and FIG. 6.

4-epi minocycline: 0.12% in area (HPLC)
Melting point: 193° C.

Example 6

Preparation of Amorphous Minocycline Base

A solution of minocycline base in dichloromethane, isopropyl acetate or methyl tert-butyl ether was isolated by spray drying in conventional spray drying equipment using an inlet temperature between 45° C. and 105° C., and an outlet temperature between 30° C. and 75° C.

The isolated product can be used directly to obtain any of the Forms of crystalline minocycline base or can be subjected to a post drying step under vacuum at about 45° C. to yield pure amorphous minocycline base.

Yield: 24.5 g
HPLC purity: 98.6% in area

The XRPD pattern and Infra red are presented in FIG. 7 and FIG. 8.

What is claimed is:

1. A process for preparing amorphous minocycline base, which process comprises spray drying a solution or suspension of minocycline in an organic solvent.

2. A process according to claim 1, wherein the solvent is methyl tert-butyl ether, dichloromethane or isopropyl acetate.

3. A process according to claim 1, further including drying the amorphous minocycline base so obtained under vacuum.

4. A process according to claim 1, including drying at a temperature of from about 25° C. to about 45° C.

5. A process according to claim 1, including drying at a temperature of from about 35° C. to about 45° C.

* * * * *